United States Patent
Clancy et al.

(10) Patent No.: US 6,399,100 B1
(45) Date of Patent: *Jun. 4, 2002

(54) CONTROLLED RELEASE PHARMACEUTICAL COMPOSITIONS CONTAINING TIAGABINE

(75) Inventors: Maurice Joseph Anthony Clancy, Athlone; Kenneth Iain Cumming, Dublin; Michelle Caulfield, Ballhaunis, all of (IE)

(73) Assignee: Elan Corporation, plc, Dublin (IE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/127,210

(22) Filed: Jul. 31, 1998

Related U.S. Application Data

(60) Provisional application No. 60/054,432, filed on Aug. 1, 1997.

(51) Int. Cl.[7] ............ A61K 9/22; A61K 9/26; A61K 9/28; A61K 9/16
(52) U.S. Cl. .......... 424/468; 424/469; 424/474; 424/475; 424/486; 424/488; 424/489; 424/490; 514/772.3; 514/781
(58) Field of Search ............ 424/468, 474, 424/484, 469, 470, 480, 475, 486, 488, 489, 490

(56) References Cited

U.S. PATENT DOCUMENTS

| | | | |
|---|---|---|---|
| 4,772,615 A | 9/1988 | Pavia | 514/318 |
| 4,910,312 A | 3/1990 | Pavia | 546/227 |
| 5,010,090 A | 4/1991 | Gronvald et al. | 514/326 |
| 5,053,521 A | 10/1991 | Pavia | 548/572 |
| 5,348,965 A | 9/1994 | Andersen et al. | 514/325 |
| 5,354,760 A | 10/1994 | Petersen et al. | 514/326 |

FOREIGN PATENT DOCUMENTS

| | | |
|---|---|---|
| WO | WO 87/00171 | 1/1987 |
| WO | WO 95/29665 | 11/1995 |
| WO | WO 95/31976 | 11/1995 |
| WO | WO 96/34606 | 11/1996 |
| WO | WO 97/02813 | 1/1997 |
| WO | WO 97/43902 | 11/1997 |
| WO | WO 97/47619 | 12/1997 |
| WO | WO 98/05330 | 2/1998 |

*Primary Examiner*—James M. Spear
(74) *Attorney, Agent, or Firm*—Caesar, Rivise, Bernstein, Cohen & Pokotilow, Ltd.

(57) ABSTRACT

Controlled release oral pharmaceutical preparations are provided which comprise a therapeutically effective amount of tiagabine or a pharmaceutically acceptable salt thereof dispersed in a rate controlling polymeric matrix comprising at least one rate controlling polymer. The preparation can be formulated into oral dosage forms such as tablets or multiparticulates which provide therapeutically effective plasma levels of tiagabine for a period of at least 12 hours, preferably 24 hours or more. The preparation can provide tiagabine mean plasma concentrations equal to or greater than 50% of the maximum plasma concentration for at least 10 hours, preferably 14 hours, most preferably 16 hours or more.

27 Claims, 2 Drawing Sheets

CONTROLLED RELEASE PHARMACEUTICAL COMPOSITIONS CONTAINING TIAGABINE

This application claims the benefit of Provisional Application No. 60/054,432 filed Aug. 1, 1997.

FIELD OF THE INVENTION

This invention relates to controlled release tiagabine formulations and in particular to matrix delivery systems for providing oral controlled release tiagabine formulations, including once or twice daily formulations.

BACKGROUND OF THE INVENTION

The anti-epileptic drug tiagabine hydrochloride, a nipecotic acid derivative linked to a lipophilic anchor which enables it to cross the blood-brain barrier, potently and specifically inhibits uptake of the inhibitory neurotransmitter γ-aminobutyric acid (GABA) into astrocytes and neurons. Tiagabine is primarily under investigation as an anticonvulsant agent, but the compound is also reported to possess anxiolytic activity and may be beneficial in the treatment and prevention of tardive dyskinesia. Tiagabine has shown broad activity against a range of seizure types, including drug-induced, electroshock-induced, light-induced, amygdala-kindled, and audiogenic and has been approved in a number of countries for add-on treatment of adult epileptic patients with complex partial seizures. It is well tolerated and does not cause withdrawal effects or displace other drugs. In humans, tiagabine absorption is rapid and complete. It is metabolized in the liver with a linear process of elimination and a half-life of 5–8 hours. Although tiagabine does not induce or inhibit metabolic processes, it can provide a target for enzyme inducers that can lower its elimination half-life to 2–3 hours. Conventional formulations of tiagabine, such as 10 mg formulations, are dosed t.i.d. or q.i.d.

Published information regarding therapeutic plasma levels for tiagabine include Leach et al. (*Seizure* 4(2):155–7, 1995), which reports an experience with a deliberate overdose of tiagabine. Plasma levels were 3.1 μg/ml four hours after ingestion which is 30 times higher than typical steady state therapeutic dosing levels. Sachdeo et al. (*Archives of Neurology* 54(5):595–601, 1997) evaluated 2 regimens for tiagabine dosing, 16 mg b.i.d. or 8 mg q.i.d. (34 mg/day), as add-on therapy for patients with complex partial seizures. Schacter (*Epilepsia* 36 Suppl 6:S2–26, 1995) assessed tiagabine monotherapy in patients with partial seizures. In a dose-ranging study, the mean final dose was 38.4 mg/day (range: 24–54 mg/day) for patients who converted to tiagabine monotherapy. In a low (6 mg/day) versus high (36 mg/day) dose study, median 4-week complex partial seizure rates decreased significantly in patients from both dose groups but significantly more patients in the high-dose group experienced a reduction in seizures of at least 50% compared with the low-dose group.

U.S. Pat. No. 5,010,090 discloses a class of novel compounds, including tiagabine, and their pharmaceutically acceptable salts that exhibit GABA-uptake inhibitory properties useful for the treatment of epilepsy and other CNS related diseases. U.S. Pat. No. 5,354,760 discloses crystalline tiagabine hydrochloride monohydrate and a process for preparing the same. WO 96/34606 discloses tiagabine hydrochloride compositions which include an antioxidant such as α-tocopherol to stabilize the tiagabine. Despite the relatively short elimination half-life for tiagabine in humans and the concomitant need to administer the drug several times per day, none of these patents address the additional benefits possible from a controlled-release formulation for tiagabine such as enhanced patient compliance or improved therapeutic results.

WO 95/29665 discloses a slow-release extended antiepileptic drug dosage form that has an exit in the dosage form for releasing the antiepileptic drug and a lamina between the dosage form wall and the antiepileptic drug formulation to maintain the integrity of the dosage form during the delivery of the antiepileptic drug to the patient. Additionally, this application discloses a diffusion-dosage form that releases a drug by membrane-controlled diffusion, a bioerodible dosage form and a ion-exchange dosage form for administration of antiepileptic drugs selected from the group consisting of hydantoins, barbiturates, deoxybarbiturates, iminostilbenes, succinimides, oxazolidinediones and benzodiazepines. Examples for the antiepileptic drugs phenytoin, carbamazepine, and ethotoin are provided.

Controlled-release therapeutic dosage forms for tiagabine in which the medicinal substance is incorporated into a matrix would be desirable per se on account of the ease of their manufacture, the low degree of variation between different manufacturing processes and because of the relatively low costs. Ideally, not only should the dosage form control release of the tiagabine in such a manner that an effective concentration in the blood can be maintained over an extended period of time, but also the drug release should be such that the drug concentration in the blood remains relatively constant over the extended period of time to improve therapeutic results and/or minimize side effects. Thus, there exists a need for a controlled-release tiagabine formulation having these properties, especially one having minimal $C_{max}$ to $C_{min}$ peak to trough variations over a period of at least either 12 or 24 hours.

SUMMARY OF THE INVENTION

It is an object of the present invention to provide controlled release oral dosage forms for tiagabine which provide therapeutic levels of tiagabine for a period of at least 12 hours, preferably 24 hours or longer.

It is a further object of the present invention to provide controlled release oral dosage forms for tiagabine which provide a tiagabine plasma concentration equal to or greater than 50% of the maximum plasma concentration ($C_{max}$) for at least 10 hours, preferably 15 hours, most preferably 20 hours or more. Preferably, the maximum plasma concentration minus the minimum plasma concentration divided by the average plasma concentration $[(C_{max}-C_{min})/C_{av}]$ taken over a period of at least 12 hours, preferably 24 hours, is less that 0.80, more preferably less than 0.60.

It is yet a further object of the present invention to provide controlled release oral dosage forms for tiagabine which provide therapeutic levels of tiagabine for a period of at least 12 hours, preferably 24 hours, having a mean in vitro dissolution profile in aqueous media at 37° C. such that about 5 5 to 40% of the tiagabine is released after 1 hour; about 25–65% is released after 4 hours; about 55–95% is released after 10 hours and about 80–100% is released after 22 hours when measured according to the USP Apparatus II (paddles) method. More preferably, the in vitro dissolution profile shows release of about 10 to 30% tiagabine after 1 hour; 30 to 60% release after 4 hours; 60 to 90% release after 10 hours and 85 to 100% release after 22 hours.

The above-mentioned objects and others are achieved by virtue of the present invention, which provides a controlled release preparation comprising a therapeutically effective amount of tiagabine dispersed in a rate controlling polymeric matrix comprising at least one rate controlling polymer. It is found that incorporation of tiagabine in the polymeric matrixes according to this invention allows for effective control over the release of tiagabine over time such that administration of the preparation achieves therapeutic levels of tiagabine over extended periods of time in humans, such as for at least 12 hours, and in certain preferred embodiments, for 24 hours or longer.

The applicants have found in the case of the formulations of the present invention that therapeutically effective blood levels of tiagabine can be maintained substantially over 24 hours with peak plasma levels occurring between 2 and 18 hours, preferably between 4 and 16 hours, most preferably between 6 and 14 hours.

The rate controlling polymer preferably includes a hydroxypropyl-methylcellulose (HPMC), a hydroxypropylcellulose (HPC), a poly(ethylene oxide), an ethylcellulose or a combination thereof present in an amount of 5 to 75% by weight, more preferably 20 to 50% by weight, most preferably 30 to 45% by weight in the preparation.

An especially preferred type of HPMC for use in accordance with the invention is an HPMC sold under the trademark Methocel (Dow Chemical Co.) or equivalents. Suitable Methocels include the K grades such as Methocel K15M, Methocel K100M, Methocel K100LV and Methocel K4M. Other suitable Methocels include the E, F and J grades. An especially preferred type of HPC for use in accordance with the invention is an HPC sold under the trademark Klucel (Hercules, Inc.) or equivalents. Suitable Klucels include Klucel LF, Klucel JF, Klucel GF, Klucel MF and Klucel HF. An especially preferred type of poly (ethylene oxide) for use in accordance with the invention is a poly(ethylene oxide) sold under the trademark Sentry Polyox (Union Carbide Corp.) or equivalents. Suitable Polyoxs include the Polyox WSR grades such as Polyox WSR Coagulant, Polyox WSR-301, Polyox WSR-303, Polyox WSR N-12K, Polyox WSR N-60K, Polyox WSR-1105, Polyox WSR-205 and Polyox WSR N-3000. An especially preferred type of ethylcellulose for use in accordance with the invention is an ethylcellulose sold under the trademark Ethocel (Dow Chemical Co.) or equivalents.

The present invention is further related to a method treating a patient by orally administering the controlled release tiagabine preparation as set forth herein.

DETAILED DESCRIPTION OF THE INVENTION

Figure 1:
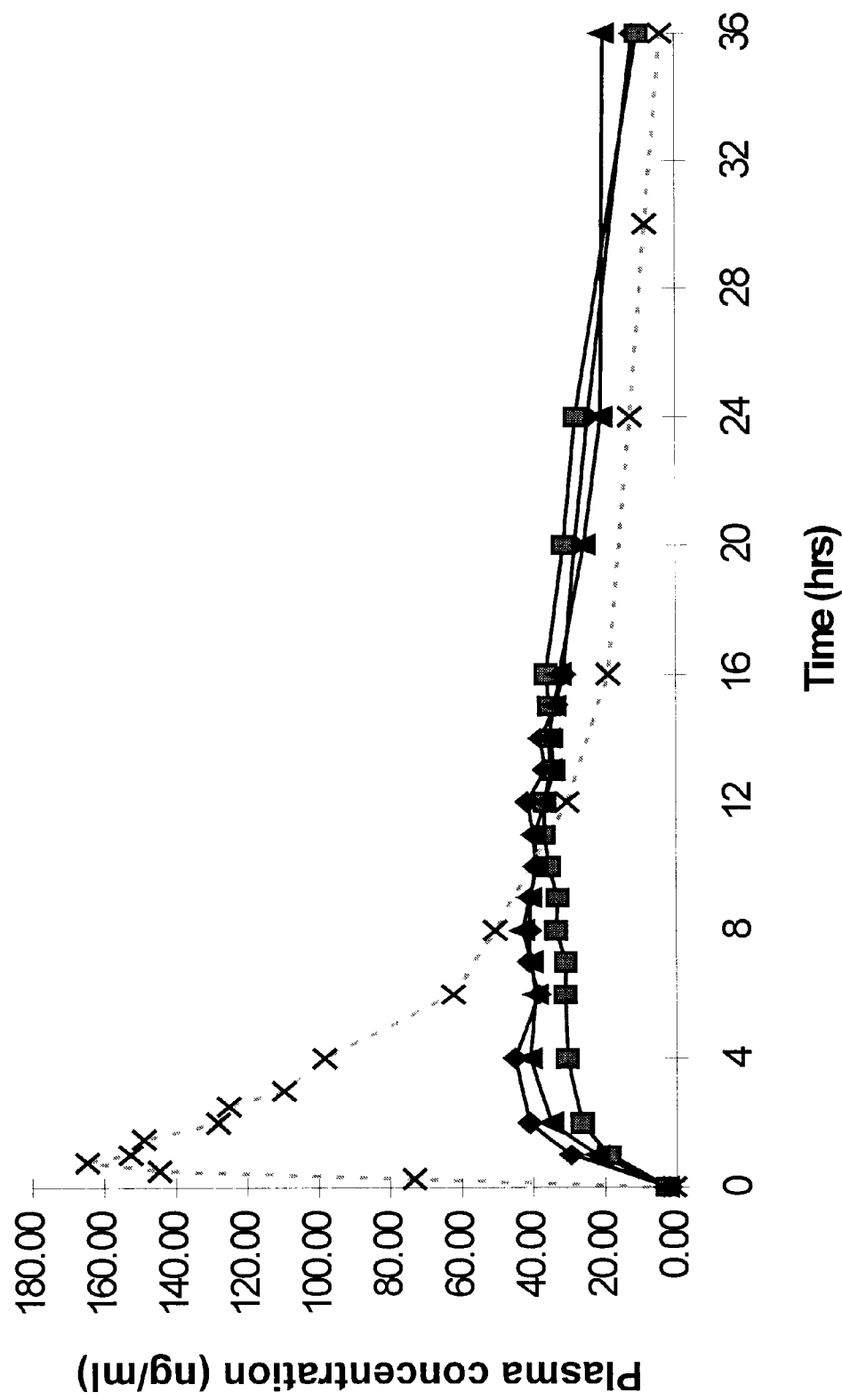
FIG. 1 shows the tiagabine plasma level concentration (ng/ml) over 36 hours following administration of the following 10 mg tiagabine formulations made according to this invention to 12 healthy male volunteers in an open label, randomized, four period cross-over study: Formulation A (——♦——) [Batch 8 of Example 4; 20% wt Methocel K15M, 10% wt Klucel LF, Direct Compression]: Formulation B (——■——) [Batch 21 of Example 9, 30% wt Methocel K15M, 15% wt Klucel LF, Melt Granulation Type B]; and Formulation C (——▲——) [Batch 22 of Example 9, 20% wt Methocel K15M, 10% wt Klucel LF, Melt Granulation Type B]. The control for this study is the commercially available immediate release tiagabine 10 mg Gabitril® tablets (Novo Nordisk) (----✗----)

The invention provides a controlled release oral pharmaceutical preparation comprising a therapeutically effective amount of tiagabine or a pharmaceutically acceptable salt thereof dispersed in a rate controlling polymeric matrix comprising at least one rate controlling polymer, which preparation provides therapeutically effective plasma levels of tiagabine for a period of at least 12 hours, preferably 24 hours or more.

As used herein, the term "tiagabine" refers to N-(4,4-di (3-methylthien-2-yl)but-3-enyl) nipecotic acid, including the R and S isomers and racemic mixtures, or a pharmaceutically acceptable salt thereof. The preferred pharmaceutically acceptable salt is the hydrochloride salt. The R isomer of N-(4,4-di(3-methylthien-2-yl)but-3-enyl) nipecotic acid is preferred and the monohydrate crystalline form of the R isomer of N-(4,4-di(3-methylthien-2-yl)but-3-enyl) nipecotic acid hydrochloride is the most preferred form of tiagabine.

By "controlled release" it is meant for purposes of the present invention that therapeutically active tiagabine is released from the preparation at a controlled rate such that therapeutically beneficial blood levels (but below toxic levels) of tiagabine are maintained over an extended period of time, e.g., providing a 12 hour or a 24 hour dosage form.

The term "rate controlling polymer" as used herein includes hydrophilic polymers, hydrophobic polymers or mixtures of hydrophilic and/or hydrophobic polymers that are capable of retarding the release of tiagabine in vivo when tiagabine is dispersed in a polymeric matrix formed from the rate controlling polymers. Examples of rate controlling polymers to be used in this invention include hydroxyalkylcellulose, such as hydroxypropylcellulose and hydroxypropylmethylcellulose; poly(ethylene)oxide; alkylcellulose such as ethycellulose and methylcellulose; carboxymethylcellulose; hydrophilic cellulose derivatives; polyethylene glycol; polyvinylpyrrolidone; cellulose acetate; cellulose acetate butyrate; cellulose acetate phthalate; cellulose acetate trimellitate; polyvinylacetate phthalate; hydroxypropylmethylcellulose phthalate; hydroxypropylmethylcellulose acetate succinate; poly(alkyl methacrylate); and poly (vinyl acetate). Other suitable hydrophobic polymers include polymers or copolymers derived from acrylic or methacrylic acid esters, copolymers of acrylic and methacrylic acid esters, zein, waxes, shellac and hydrogenated vegetable oils.

The hydroxypropylmethylcelluloses used according to the invention preferably have a viscosity (2 wt % solution at 20° C.) of about 100 to 100,000 cps, preferably 100 to 30,000 cps. Especially suitable are Methocel K types or their equivalents. The hydroxypropylcelluloses used according to the invention preferably have a molecular weight of about 80,000 to 1,150,000, more preferably 80,000 to 600,000. Especially suitable is Klucel LF, which has a molecular weight of 100,000. The poly(ethylene oxide) used according to the invention preferably has a molecular weight of about 100,000 to 7,000,000, more preferably 900,000 to 7,000, 000. Especially suitable is Polyox WSR Coagulant, which has a molecular weight of 5,000,000. The ethylcelluloses used according to the invention preferably have a viscosity of about 3 to 110 cps, more preferably 7 to 100 cps.

To ensure correct release kinetics, the controlled release preparation of this invention contains about 5 and 75% by weight, preferably about 20 and 50% by weight, more preferably about 30 to 45% by weight rate controlling polymer(s) and about 1 to 40% by weight, preferably about 3 to 25% by weight tiagabine.

The controlled release preparation according to the invention can preferably include auxiliary agents, such as diluents, lubricants and/or melting binders. Preferably, the excipients are selected to minimize the water content of the preparation. Preferably, the preparation includes an antioxidant.

Suitable diluents include pharmaceutically acceptable inert fillers such as microcrystalline cellulose, lactose, dibasic calcium phosphate, saccharides, and/or mixtures of any of the foregoing. The diluent is suitably a water soluble diluent. Examples of diluents include microcrystalline cellulose such as Avicel ph112, Avicel pH101 and Avicel pH102; lactose such as lactose monohydrate, lactose anhydrous, and Pharmatose DCL 21; dibasic calcium phosphate such as Emcompress; mannitol; starch; sorbitol; sucrose; and glucose. Diluents are carefully selected to match the specific formulation with attention paid to the compression properties. The diluent is preferably used in an amount of 10 to 90% by weight, preferably 25 to 65% by weight, of the controlled release preparation.

Suitable lubricants, including agents that act on the flowability of the powder to be compressed are, for example, colloidal silicon dioxide such as Aerosil 200; talc; stearic acid, magnesium stearate, and calcium stearate.

Suitable low temperature melting binders include polyethylene glycols such as PEG 6000; cetostearyl alcohol; cetyl alcohol; polyoxyethylene alkyl ethers; polyoxyethylene castor oil derivatives; polyoxyethylene sorbitan fatty acid esters; polyoxyethylene stearates; poloxamers; and waxes.

To improve the stability of the tiagabine in the controlled release preparation, an antioxidant compound can be included. Suitable antioxidants include sodium metabisulfite; tocopherols such as $\alpha$, $\beta$, or $\delta$-tocopherol tocopherol esters and $\alpha$-tocopherol acetate; ascorbic acid or a pharmaceutically acceptable salt thereof; ascorbyl palmitate; alkyl gallates such as propyl gallate, Tenox PG, Tenox s-1; sulphites or a pharmaceutically acceptable salt thereof; BHA; BHT; and monothioglycerol.

The controlled release preparation according to the invention preferably can be manufactured by blending tiagabine with the rate controlling polymer(s) and auxiliary excipients followed by direct compression. Other methods for manufacturing the preparation include melt granulation. Preferred melt granulation techniques include melt granulation of tiagabine together with the rate controlling polymer(s) and diluent(s) followed by compression of the granules and melt granulation of the tiagabine with subsequent blending of the tiagabine melt granules with the rate controlling polymer(s) and diluents followed by compression of the blend. As desired prior to compression, the blend and/or granulate can be screened and/or mixed with auxiliary agents until an easily flowable homogeneous mixture is obtained.

Oral dosage forms of the controlled release preparation according to the invention can be in the form of tablets or can be multiparticulate, such as in the form of pellets or mini-tablets. If desired, capsules such as hard or soft gelatin capsules, can contain the multiparticulates. If desired, the multiparticulate oral dosage forms can comprise a blend of at least two populations of pellets or mini-tablets having different controlled-release in vitro and/or in vivo tiagabine release profiles. If desired, one of the pellet or mini-tablet populations can comprise immediate release tiagabine multiparticulates, such as multiparticulates formed by conventional means.

If desired, the controlled release matrix tablets or multiparticulates of this invention can be coated with a controlled release polymer layer so as to provide additional controlled release properties. Suitable polymers that can be used to form this controlled release layer include the rate controlling polymers listed above.

As desired, the tablets, pellets or mini-tablets according to the invention can be provided with a light-protective and/or cosmetic film coating, for example, film-formers, pigments, anti-adhesive agents and plasticisers. Such a film former may consist of fast-dissolving constituents, such as low-viscosity hydroxypropylmethylcelluose, for example Methocel E5 or D14 or Pharmacoat 606 (Shin-Etsu). The film coating may also contain excipients customary in film-coating procedures, such as light-protective pigments, for example iron oxide, or titanium dioxide, anti-adhesive agents, for example talc, and also suitable plasticisers such as PEG 400, PEG 6000, diethyl phthalate or triethyl citrate.

Preferably, oral dosage forms according to the invention are suitable for twice-daily or, more preferably, once-daily administration of tiagabine. For example, once-daily oral dosage forms may contain from about 5 to 100 mg tiagabine, preferably 10 to 50 mg tiagabine, and most preferably 20 to 40 mg tiagabine to provide a therapeutic amount of tiagabine throughout the day in a controlled release fashion.

The rate controlling polymeric matrix of this invention may consist of a hydrogel matrix. For instance, tiagabine can be compressed into a dosage form containing a rate controlling polymer, such as HPMC, or mixture of polymers which when wet will swell to form a hydrogel. The rate of release of tiagabine from this dosage form is controlled both by diffusion from the swollen tablet mass and by erosion of the tablet surface over time. The rate of release of the tiagabine may be controlled both by the amount of polymer per tablet and by the inherent viscosities of the polymers used.

The tiagabine employed in the following examples is the monohydrate crystalline form for the hydrochloride salt of the R isomer. The raw material tiagabine hydrochloride monohydrate has high aqueous solubility and consists of fine needle shaped crystals which are relatively cohesive and do not provide good flow properties.

EXAMPLE 1

Direct Compression

Powder blends of tiagabine, the rate controlling polymer(s), and, if present, filler(s), diluent(s), lubricant(s) and/or antioxidation agent(s) are blended such as in a V-cone blender and tablet compression is carried out on a single station table press or a rotary tablet press, such as a Fette E1 rotary tablet press (Wilhelm Fette GMBH) for small scale production or a Horn (Horn of Noack Pharmatechnic GMBH) rotary table press or Fette P1000 for larger scale production. The dissolution rate for the resulting tablets is measured using USP Apparatus II (paddles) at 50 r.p.m. with 900 ml deionized water at 37° C. as the dissolution media.

EXAMPLE 2

Direct Compression Formulations

Controlled release formulations having 30 mg tiagabine in 300 mg tablets and employing a variety of rate controlling polymers are prepared according to the small scale production procedures given in Example 1. Table 1 shows the formulation details and dissolution profiles for these formulations, which all exhibit controlled release over a 12 to 24-hour period. The release rates for the formulations containing different Methocel grades show rank order of K100LV (low viscosity)>K15M (intermediate viscosity) >K100M (high viscosity) while the release profile for the formulation containing Polyox, which has a relatively low moisture content compared to the Methocels, is almost equivalent to that of the K15M grade of Methocel.

TABLE 1

| Batch | 1 | 2 | 3 | 4 |
|---|---|---|---|---|
| Material | % wt | % wt | % wt | % wt |
| Tiagabine HCl Monohydrate | 11.50 | 11.50 | 11.50 | 11.50 |
| Methocel K15M | 20.00 | — | — | — |
| Methocel K100M | — | — | 20.00 | — |
| Methocel K100LV | — | 20.00 | — | — |
| Polyox WSR | — | — | — | 20.00 |
| Klucel LF | 10.00 | 10.00 | 10.00 | 10.00 |
| Talc | 5.00 | 5.00 | 5.00 | 5.00 |
| Aerosil 200 | 0.20 | 0.20 | 0.20 | 0.20 |
| Sodium Metabisulphite | 0.25 | 0.25 | 0.25 | 0.25 |
| Avicel pH112 | 53.05 | 53.05 | 53.05 | 53.05 |

| Dissolution Profile (hrs) | MEAN % REL. | MEAN % REL. | MEAN % REL. | MEAN % REL. |
|---|---|---|---|---|
| 0.5 | 12.7 | 20.0 | 9.5 | 10.1 |
| 1 | 19.2 | 27.9 | 16.0 | 15.3 |
| 2 | 28.2 | 39.9 | 24.2 | 23.6 |
| 4 | 40.8 | 56.5 | 35.5 | 37.0 |
| 8 | 58.5 | 78.9 | 51.1 | 56.8 |
| 12 | 71.7 | 87.1 | 63.0 | 70.6 |
| 24 | 90.2 | 94.0 | 83.5 | 89.8 |

EXAMPLE 3

Direct Compression Formulations

Controlled release formulations having 10 mg tiagabine in 300 mg tablets and employing different types of diluents are prepared according to the small scale production procedures given in Example 1. Table 2 shows the formulations details and dissolution profiles for these formulations, which all exhibit controlle release over a 12 to 24-hour period.

TABLE 2

| Batch | 5 | 6 | 7 |
|---|---|---|---|
| Material | % wt | % wt | % wt |
| Tiagabine HCl Monohydrate | 3.82 | 3.82 | 3.82 |
| Methocel K15M | 10.00 | 10.00 | 10.00 |
| Methocel K100LV | 8.00 | 8.00 | 8.00 |
| Emcompress Anhydrous | — | — | 72.73 |
| Avicel pH 112 | — | 72.73 | — |
| Lactose | 72.73 | — | — |
| Talc | 5.00 | 5.00 | 5.00 |
| Aerosil 200 | 0.20 | 0.20 | 0.20 |
| Sodium Metabisulphite | 0.25 | 0.25 | 0.25 |

TABLE 2-continued

| Batch | 5 | 6 | 7 |
|---|---|---|---|
| Dissolution Profile (hrs) | MEAN % REL. | MEAN % REL | MEAN % REL. |
| 0.5 | 18.9 | 29.1 | 15.8 |
| 1 | 27.6 | 38.4 | 23.2 |
| 2 | 40.9 | 51.5 | 33.6 |
| 4 | 58.9 | 64.5 | 47.4 |
| 8 | 82.2 | 79.4 | 66.5 |
| 12 | 89.8 | 87.7 | 78.8 |
| 24 | 90.6 | 92.6 | 92.2 |

EXAMPLE 4

Direct Compression Formulations

Controlled release formulations having 10 mg tiagabine in 300 mg tablets and employing different rate controlling polymers are prepared according to the larger scale production procedures given in Example 1. Table 3 shows the formulation details and dissolution profiles for these controlled release formulations.

EXAMPLE 5

Melt Granulation Type A—Diluent(s)/Matrix Polymer(s) added intragranularly

Tiagabine, the low temperature melting binder(s), the rate controlling polymer(s) and, if desired, filler(s), diluent(s) and/or antioxidation agent(s) are blended such as in a Gral 25L high speed granulator (GEI Collette) prior to the start of the melt process. The melt granulation is carried out with a thermal jacket and, if desired, under a nitrogen blanket. If desired, components such as the antioxidant α tocopherol can be added to the Gral bowl once the melt temperature has been reached. After the bowl temperature is lowered, lubricant(s) such as talc can be added. The resulting blend is tabletted and the dissolution rate for the tablets is measured using USP Apparatus II (paddles) at 50 r.p.m. with 900 ml deionized water at 37° C. as the dissolution media.

TABLE 3

| Batch | 8 | 9 |
|---|---|---|
| Material | % wt | % wt |
| Tiagabine HCl.H$_2$O | 3.83 | 3.83 |
| Methocel k15M | 20 | — |
| Methocel K100LV | — | 25 |
| Klucel LF | 10 | 10 |
| Avicel pH112 | 60.53 | 55.53 |
| Aerosil 200 | 0.4 | 0.4 |
| Talc USP | 5.0 | 5.0 |
| Sodium Metabisulfite | 0.25 | 0.25 |
| Theoretical potency (mg/tab) | 10 | 10 |
| Punch size/shape | 14 × 7 mm scored oval | 14 × 7 mm scored oval |
| Mean Tablet Hardness (N) | 106 | 118 |

| Dissolution Profile (hrs) | MEAN % RELEASE | MEAN % RELEASE |
|---|---|---|
| 0.5 | 18.4 | 19.2 |
| 1 | 28.0 | 26.3 |
| 2 | 39.8 | 36.8 |
| 4 | 54.2 | 55.5 |
| 6 | 63.2 | 69.3 |

TABLE 3-continued

| Batch | 8 | 9 |
|---|---|---|
| 8 | 69.6 | 76.6 |
| 10 | 74.7 | 81.5 |
| 16 | 85.0 | — |
| 22 | 89.0 | 91.3 |

EXAMPLE 6

Melt Granulation Formulations—Type A

Controlled release formulations having 10 mg tiagabine in 300 mg tablets containing 20% wt and 30% wt Methocel K15M are prepared according to the procedures given in Example 5. Table 4 shows the formulation details and dissolution profiles for these controlled release formulations.

TABLE 4

| Batch | 10 | 11 | 12 | 13 |
|---|---|---|---|---|
| Material | % wt | | % wt | |
| Tiagabine HCl.H$_2$O | 3.83 | | 3.83 | |
| PEG 6000 | 6.25 | | 6.25 | |
| Methocel K15M | 20.00 | | 30.00 | |
| Klucel LF | 10.10 | | 15.00 | |
| Pharmatose DCL 21 Lactose Monohydrate | 10.78 | | 10.78 | |
| Avicel pH112 | 43.31 | | 28.81 | |
| α-Tocopherol | 0.33 | | 0.33 | |
| Talc USP | 5.00 | | 5.00 | |
| Theoretical potency (mg/tab) | 10 | 10 | 10 | 10 |
| Punch size/shape | 13 × 8 mm oval | 14 × 7 mm caplet | 13 × 8 mm oval | 14 × 7 mm caplet |
| Mean Tablet Hardness (N) | 50.1 | 40.3 | 47.3 | 40.3 |
| Dissolution Profile (hrs) | Mean % Rel. | Mean % Rel. | Mean % Rel. | Mean % Rel. |
| 0.5 | 9.1 | 10.5 | 8.3 | 8.3 |
| 1 | 13.8 | 15.5 | 12.6 | 13.1 |
| 2 | 20.9 | 23.4 | 19.1 | 20.3 |
| 4 | 31.3 | 35.7 | 28.9 | 31.6 |
| 8 | 49.0 | 57.2 | 45.0 | 51.1 |
| 12 | 63.9 | 73.9 | 59.6 | 67.2 |
| 24 | 91.6 | 98.4 | 89.3 | 98.7 |

EXAMPLE 7

Melt Granulation Type B—Diluent(s)/Matrix Polymers(s) Added Extragranularly

Tiagabine and other pharmaceutical excipients such as low temperature melting binders and optionally an antioxidant(s) are blended such as in a 24L Gral high speed granulator prior to the start of the melt process. The melt granulation is carried out with a thermal jacket and, if desired, under a nitrogen blanket. If desired, components such as the antioxidant α-tocopherol are added to the Gral bowl once the melt temperature has been reached. Following melt granulation, the cooled granulate can optionally be screened such as by passing it through a sieve. The granulate is blended with the diluent(s), rate controlling polymers(s) and, optionally other excipients such as silicon dioxide and talc. The resulting blend is tabletted and the dissolution rate for the tablets is measured using USP Apparatus II (paddles) at 50 r.p.m. with 900 ml deionized water at 37° C. as the dissolution media.

EXAMPLE 8

Melt Granulation Formulations—Type B

Controlled release formulations having 10 mg tiagabine in 300 mg tablets containing Methocel K15M or Polyox WSR are prepared according to the procedures given in Example 7 and tabletted using a Fette E1 single station tablet press. The tiagabine granulate for Batches 14–17 was screened through a 600 μm sieve prior to tableting. Table 5 shows the formulation dissolution profiles for these controlled release formulations.

TABLE 5

| | Batch | | | | | | |
|---|---|---|---|---|---|---|---|
| | 14 | 15 | 16 | 17 | 18 | 19 | 20 |
| Tiagabine Granulate | | | | % wt | | | |
| Tiagabine HCl.H$_2$0 | | | | 23.95 | | | |
| PEG 6000 | | | | 6.25 | | | |
| α-Tocopherol | | | | 2.395 | | | |
| Anhydrous Lactose | | | | 67.405 | | | |
| Materials | % wt | % wt | % wt | % wt | % wt | % wt | % wt |
| Tiagabine granulate | 15.987 | 15.987 | 15.987 | 15.98 | 15.987 | 15.987 | 15.987 |
| Methocel K15M | 20.00 | 20.00 | 30.00 | 30.00 | 20.00 | 30.00 | — |
| Polyox WSR | — | — | — | — | — | — | 20.00 |
| Klucel LF | 10.00 | 10.00 | 15.00 | 15.00 | 10.00 | 15.00 | 10.00 |
| Talc | 5.00 | 5.00 | 5.00 | 5.00 | 5.00 | 5.00 | 5.00 |
| Aerosil 200 | 0.40 | 0.40 | 0.40 | 0.40 | — | — | — |
| Avicel pH112 | 48.613 | 48.613 | 33.613 | 33.613 | 49.013 | 34.01 | 49.013 |
| Theoretical potency | 10 | 10 | 10 | 10 | 10 | 10 | 10 |

TABLE 5-continued

| | Batch | | | | | | |
|---|---|---|---|---|---|---|---|
| | 14 | 15 | 16 | 17 | 18 | 19 | 20 |
| Punch size/shape | 13 × 8 mm oval | 14 × 7 mm caplet | 13 × 8 mm oval | 14 × 7 mm caplet | 13 × 8 mm oval | 13 × 8 mm oval | 13 × 8 mm oval |
| Mean Tab. Hardness | 93.5 | 93.0 | 102.2 | 89.6 | 101.5 | 102.1 | |
| Dissolution Profile (hrs) | Mean % Rel. | Mean % Rel. | Mean % Rel. | Mean % Rel. | Mean % Rel. | Mean % Rel. | Mean % Rel. |
| 0.5 | 11.6 | 11.9 | 7.8 | 7.6 | 19.3 | 7.8 | 11.4 |
| 1 | 17.0 | 15.1 | 12.0 | 11.5 | 26.2 | 11.5 | 16.5 |
| 2 | 26.3 | 22.9 | 17.9 | 17.5 | 31.6 | 17.8 | 26.1 |
| 4 | 40.6 | 35.6 | 27.1 | 27.2 | 56.3 | 31.6 | 42.9 |
| 8 | 59.7 | 53.8 | 41.2 | 43.0 | 73.0 | 50.0 | 61.5 |
| 12 | 73.1 | 67.0 | 52.2 | 55.3 | 83.3 | 66.6 | 73.2 |
| 24 | 92.2 | 86.9 | 72.6 | 76.4 | 93.6 | 94.7 | 85.8 |

EXAMPLE 9

Melt Granulation Formulations—Type B

Controlled release formulations having 10 mg tiagabine in 300 mg tablets containing Methocel k15M or Polyox WSR are prepared according to the procedures given in Example 7. Batches 21 and 22 were screened through a 600 μm sieve and tabletted using a Horn rotary tablet press. Table 6 shows the formulation details and dissolution profiles for these controlled release formulations.

TABLE 6

| Batch | 21 | 22 |
|---|---|---|
| Tiagabine Granulate | % wt | |
| Tiagabine HCl.H₂O | 23.88 | |
| PEG 6000 | 6.25 | |
| α-Tocopherol Acetate | 2.388 | |
| Pharmatose DC L21 | 67.482 | |
| Materials | % wt | % wt |
| Tiagabine granulate | 16 | 16 |
| Methocel K15M | 30 | 20 |
| Klucel LF | 15 | 10 |
| Talc | 5.0 | 5.0 |
| Aerosil 200 | 0.4 | 0.4 |
| Avicel pH112 | 33.6 | 48.6 |
| Theoretical potency (mg/tab) | 10 | 10 |
| Punch size/shape | 14 × 7 mm scored oval | 14 × 7 mm scored oval |
| Mean Tab. Hardness | 94 | 99 |
| Dissolution Profile (hrs) | MEAN % RELEASE | MEAN % RELEASE |
| 0.5 | 8.1 | 11.7 |
| 1 | 13.2 | 16.3 |
| 2 | 21.8 | 28.8 |
| 4 | 35.0 | 44.8 |
| 6 | 46.5 | 57.8 |
| 8 | 57.4 | 68.3 |
| 10 | 66.4 | 85.5 |
| 16 | 88.1 | |
| 22.0 | 99.0 | 103.1 |

EXAMPLE 10

Bioavailability Study

An open label, randomized, four period cross-over study was undertaken in 12 healthy male Caucasian volunteers aged 18 to 45 (11 subjects completed) evaluating the bioavailability of three controlled release 10 mg tiagabine tablet formulations A, B and C made according to this invention compared to a 10 mg conventional instant release tablet formulation D (Gabitril®; Novo Nordisk). Dosing occurred after an overnight fast and four hours prior to meal. Blood samples were collected up to 36 hours post dosing with one week washout period separating the doses. All blood samples were collected in heparinized tubes, stored immediately at 4° C. and centrifuged within an hour. After separation, the plasma was stored at −18° C. or below pending assay. Plasma samples were assayed using a validated HPLC-assay.

FIG. 1 shows the plasma concentration of tiagabine following administration of formulation A (Batch 8 of Example 4), formulation B (Batch 21 of Example 9), formulation C (Batch 22 of Example 9) and formulation D (Gabitril®). Non-compartmental pharmacokinetic analysis of the plasma concentration data resulted in the parameters presented in Table 7. The time during which the plasma concentration was greater than 50% of the maximum plasma concentration (mean $T_{50}$) for formulations A, B and C was calculated to be 22.7 hours, 24.7 hours and 21.1 hours, respectively. Formulations A, B and C provide a good extension of plasma drug levels with little loss in relative bioavailability compared to the reference immediate release product. Additionally, these controlled release products effect minimal peak to trough fluctuations in tiagabine blood plasma levels.

TABLE 7

| Formulation | N | $C_{max}$ (ng/ml) | $t_{max}$ (h) | $AUC_{0-36}$ (ng · h/ml) | $t_{½}$ (h) |
|---|---|---|---|---|---|
| A | 11 | 52.5 ± 12.2 | 8.27 ± 3.72 | 1203 ± 297 | 10.5 |
| B | 11 | 43.7 ± 10.3 | 12.91 ± 4.55 | 1255 ± 325 | 11.7 |
| C | 11 | 51.2 ± 1.2 | 7.91 ± 5.38 | 1136 ± 360 | 8.9 |
| D | 11 | 191 ± 49.4 | 0.77 ± 0.31 | 1337 ± 272 | 9.3 |

Figure 2:
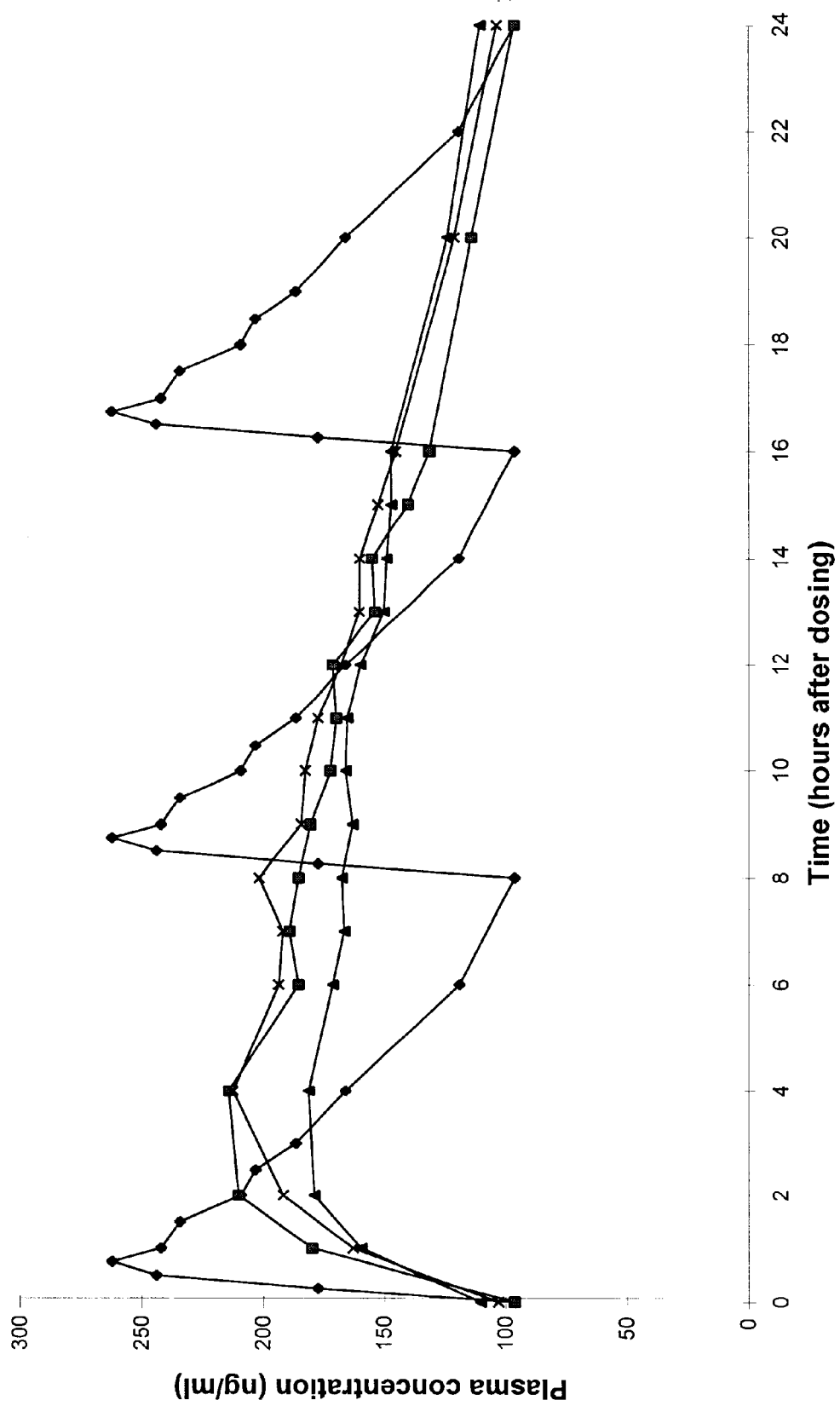
FIG. 2 illustrates projected steady state plasma tiagabine profiles for Formulation A (——■——) ) [Batch 8 of Example 4; 20% wt Methocel K15M, 10% wt Klucel LF, Direct Compression]: Formulation B (——▲——) [Batch of Example 9, 30% wt Methocel K15M, 15% wt Klucel LF, Melt Granulation Type B]; and Formulation C (----✗----) [Batch 22 of Example 9, 20% wt Methocel K15M, 10% wt Klucel LF, Melt Granulation Type B] at 30 mg dosing once daily compared to the conventional Formulation D (——♦——) [immediate release tiagabine 10 mg Gabitril® tablets (Novo Nordisk)] dosed 10 mg t.i.d.

Projected steady state tiagabine levels were determined based upon the mean single dose data for controlled release formulations A, B, C and D (10 mg dosing). Table 8 shows the steady state pharmacokinetic parameters based upon these projections for formulations A, B and C. FIG. 2 illustrates the projected steady state plasma tiagabine profiles for formulations A, B and C at 30 mg dosing once daily compared to the conventional formulation D dosed 10 mg t.i.d.

TABLE 8

| Parameter | Formulation A | Formulation B | Formulation C |
|---|---|---|---|
| $AUC_{ss(0-24)}$ | 1248.7 | 1125.1 | 1203.1 |
| $C_{av}$ | 52.0 | 46.9 | 50.1 |
| $C_{max}$ | 71.4 | 60.5 | 70.9 |
| $C_{min}$ | 32.1 | 36.8 | 34.3 |
| $(C_{max}-C_{min})/C_{av}$ | 0.76 | 0.51 | 0.73 |

The disclosures cited above are hereby incorporated by reference in their entireties. The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

What is claimed is:

1. A controlled release oral pharmaceutical preparation comprising a therapeutically effective amount of tiagabine or a pharmaceutically acceptable salt thereof dispersed in a rate controlling polymeric matrix comprising at least one rate controlling polymer, which preparation provides therapeutically effective plasma levels of tiagabine for a period of at least 12 hours, wherein said preparation is not coated with a controlled release polymer layer.

2. The preparation according to claim 1, wherein the preparation releases tiagabine in vivo such that the duration over which the tiagabine plasma concentration is equal to or greater than 50% of the peak plasma concentration is 10 hours or greater.

3. The preparation according to claim 1, wherein the in vivo maximum plasma concentration minus the minimum plasma concentration divided by the average plasma concentration taken over the effective period is less than 0.80.

4. The preparation according to claim 1, which preparation provides a mean dissolution profile in aqueous media such that about 5 to 40% of the tiagabine is released after 1 hour; about 25 to 65% of the tiagabine is released after 4 hours; about 55 to 95% of the tiagabine is released after 10 hours and about 80 to 100% of the tiagabine is released after 22 hours.

5. The preparation according to claim 1, wherein the preparation provides therapeutic levels of tiagabine over a 24 hour period for once-daily administration.

6. The preparation according to claim 2, wherein the duration over which the tiagabine plasma concentration is equal to or greater than 50% of the peak concentration is at least 15 hours.

7. The preparation according to claim 2, wherein the duration over which the tiagabine plasma concentration is equal to or greater than 50% of the peak concentration is at least 20 hours.

8. The preparation according to claim 3, wherein the in vivo maximum plasma concentration minus the minimum plasma concentration divided by the average plasma concentration taken over the effective period is less than 0.60.

9. The preparation according to claim 4, wherein the preparation provides a mean dissolution profile in aqueous media such that about 10 to 30% of the tiagabine is released after 1 hour; about 30 to 60% of the tiagabine is released after 4 hours; about 60 to 90% of the tiagabine is released after 10 hours and about 85 to 100% of the tiagabine is released after 22 hours.

10. The preparation according to claim 1, wherein the at least one rate controlling polymer is selected from the group consisting of hydroxypropylmethylcellulose, hydroxyalkylcellulose, alkylcellulose, poly(ethylene)oxide, carboxymethylcellulose, hydrophilic cellulose derivatives polyethylene glycols, polyvinylpyrrolidone, or mixtures thereof.

11. The preparation according to claim 1, wherein the at least one rate controlling polymer is selected from the group consisting of hydroxypropylmethylcellulose having a viscosity of about 100 to 100,000 cps, hydroxypropylcellulose having a molecular weight of about 80,000 to 1,150,000, ethylcellulose having a viscosity of about 3 to 110 cps and poly(ethylene)oxide having a molecular weight of about 100,000 to 7,000,000 or mixtures thereof.

12. The preparation according to claim 1, wherein the at least one rate controlling polymer comprises from about 5 to 75% by weight of the preparation.

13. The preparation according to claim 1, wherein the at least one rate controlling polymer comprises from about 20 to 50% by weight of the preparation.

14. The preparation according to claim 1, wherein the at least one rate controlling polymer comprises from about 30 to 45% by weight of the preparation.

15. The preparation according to claim 1, wherein the therapeutically effective amount of tiagabine or a pharmaceutically acceptable salt thereof is from about 5 to 100 mg.

16. The preparation according to claim 1, further comprising a diluent comprising from 10 to 90% by weight of the preparation.

17. The preparation according to claim 1, wherein the rate controlling polymeric matrix is a hydrogel.

18. The preparation according to claim 1, wherein the at least one rate controlling polymer comprises from 19 to 31% by weight of a hydroxypropylmethylcellulose and from 9 to 15% by weight of a hydroxypropylcellulose.

19. An oral dosage form suitable for once or twice daily administration containing the controlled release oral pharmaceutical preparation of claim 1.

20. The oral dosage form according to claim 19, which is in the form of tablets.

21. The oral dosage form according to claim 19, which is in the form of pellets or mini-tablets.

22. The oral dosage form according to claim 19, which is in the form of a blend of at least two populations of pellets or mini-tablets, wherein each population has a different controlled-release dissolution profile.

23. An oral dosage form comprising a controlled release oral pharmaceutical preparation comprising a therapeutically effective amount of tiagabine or a pharmaceutically acceptable salt thereof dispersed in a rate controlling polymeric matrix comprising at least one rate controlling polymer, which preparation provides therapeutically effective plasma levels of tiagabine for a period of at least 12 hours, wherein said preparation is enterically coated.

24. The oral dosage form according to claim 19, further comprising a light-protective or cosmetic film coated on the preparation.

25. The oral dosage form according to claim 21, further comprising immediate release pellets or mini-tablets containing tiagabine or a pharmaceutically acceptable salt thereof.

26. The oral dosage form according to claim 22, further comprising immediate release pellets or mini-tablets containing tiagabine or a pharmaceutically acceptable salt thereof.

27. A method of treating an epileptic condition comprising administering the oral dosage form of claim 19.

* * * * *